(12) United States Patent
Cima

(10) Patent No.: US 12,013,446 B2
(45) Date of Patent: Jun. 18, 2024

(54) DEVICE FOR MEASURING AN AMOUNT OF SUPERPARAMAGNETIC MATERIAL AND USE OF SUCH A DEVICE

(71) Applicant: ATWARE, Le Plessis-Robinson (FR)

(72) Inventor: Lionel Cima, Saint Cyr sur Loire (FR)

(73) Assignee: ATWARE, Le Plessis-Robinson (FR)

( * ) Notice: Subject to any disclaimer, the term of this patent is extended or adjusted under 35 U.S.C. 154(b) by 0 days.

(21) Appl. No.: 17/755,479

(22) PCT Filed: Sep. 9, 2020

(86) PCT No.: PCT/FR2020/051550
§ 371 (c)(1),
(2) Date: Apr. 29, 2022

(87) PCT Pub. No.: WO2021/084169
PCT Pub. Date: May 6, 2021

(65) Prior Publication Data
US 2024/0036125 A1    Feb. 1, 2024

(30) Foreign Application Priority Data
Oct. 31, 2019 (FR) ........................ 1912272

(51) Int. Cl.
*G01R 33/028* (2006.01)
*G01R 33/00* (2006.01)
(Continued)

(52) U.S. Cl.
CPC ....... *G01R 33/028* (2013.01); *G01R 33/0076* (2013.01); *G01N 27/745* (2013.01); *G01R 33/1276* (2013.01)

(58) Field of Classification Search
CPC ................ G01R 33/028; G01R 33/007; G01R 33/1276; G01N 27/745
(Continued)

(56) References Cited

U.S. PATENT DOCUMENTS 3,879,658 A * 4/1975 Hummel .............. G01N 27/74
324/201
5,005,001 A * 4/1991 Cordery ............. G08B 13/2477
340/572.2
(Continued)

FOREIGN PATENT DOCUMENTS

CA    2544061 A1    10/2007
EP    2787363 B1    10/2016
(Continued)

OTHER PUBLICATIONS

International Search Report for International Application No. PCT/FR2020/051550 dated Oct. 26, 2020, 3 pages.
(Continued)

*Primary Examiner* — Christopher P McAndrew
(74) *Attorney, Agent, or Firm* — TraskBritt

(57) ABSTRACT

A device for measuring an amount of superparamagnetic material comprises a pair of measuring coils and a pair of compensating coils, wherein the coils of a pair are identical to each other. The device also includes at least one direct current generator, a low-frequency generator, and a high-frequency generator, the generators being coupled to the first and second pairs to inject into each of the coils a current having a DC component, a high-frequency component and a low-frequency component, such that the magnetic fields generated by the coils of the same pair are identical. The device also comprises a detector of a component of an electric voltage set at a mixing frequency, which is a linear combination of the first and the second frequency.

20 Claims, 2 Drawing Sheets

(51) Int. Cl.
*G01R 33/12* (2006.01)
*G01N 27/74* (2006.01)

(58) Field of Classification Search
USPC .......................................................... 324/201
See application file for complete search history.

(56) References Cited

U.S. PATENT DOCUMENTS

| | | | |
|---|---|---|---|
| 7,405,555 B2* | 7/2008 | Rao ..................... | G06K 19/022 324/201 |
| 10,871,409 B2* | 12/2020 | Sipila ................. | G01R 33/0017 |
| 2004/0212362 A1* | 10/2004 | Baudendistel .......... | G01L 1/127 324/201 |
| 2007/0063692 A1* | 3/2007 | Rao ........................ | G06K 1/125 324/201 |
| 2007/0155024 A1 | 7/2007 | Miethe et al. | |
| 2009/0143665 A1 | 6/2009 | Seki et al. | |
| 2009/0243603 A1 | 10/2009 | MaKiranta et al. | |
| 2009/0270262 A1* | 10/2009 | Kim ..................... | G01R 33/035 324/201 |
| 2015/0108974 A1 | 4/2015 | Kennedy et al. | |
| 2018/0188206 A1* | 7/2018 | Augais ...................... | H01F 5/04 |

FOREIGN PATENT DOCUMENTS

| | | |
|---|---|---|
| EP | 3314248 B1 | 8/2019 |
| FR | 2491662 A1 | 4/1982 |
| FR | 3038063 B1 | 10/2018 |

OTHER PUBLICATIONS

International Written Opinion for International Application No. PCT/FR2020/051550 dated Oct. 26, 2020, 9 pages.
Krause et al., Magnetic Particle Detection by Frequency Mixing for Immunoassay Applications, Journal of Magnetism and Magnetic Materials, vol. 311, (2007), pp. 436-444.
Vourc'h et al., Neel Effect Toroidal Current Sensor, Hal Open Science, HAL Id: hal-00825789, https://hal.archives-ouvertes.fr/hal-00825789, (May 24, 2013), 5 pages.

* cited by examiner

DEVICE FOR MEASURING AN AMOUNT OF SUPERPARAMAGNETIC MATERIAL AND USE OF SUCH A DEVICE

CROSS-REFERENCE TO RELATED APPLICATIONS

This application is a national phase entry under 35 U.S.C. § 371 of International Patent Application PCT/FR2020/051550, filed Sep. 9, 2020, designating the United States of America and published as International Patent Publication WO 2021/084169 A1 on May 6, 2021, which claims the benefit under Article 8 of the Patent Cooperation Treaty to French Patent Application Serial No. FR1912272, filed Oct. 31, 2019.

TECHNICAL FIELD

The present disclosure relates to a device for measuring an amount of superparamagnetic material. It also relates to the use of a device of this kind, in particular for performing a differential measurement of amounts of superparamagnetic material.

BACKGROUND

The superparamagnetic materials have the particular feature of having a non-linear magnetic cycle B(H) when the excitation magnetic field H varies over a sufficiently extended range. B denotes the magnetic induction in the material, caused by the field H. It also has the advantage of not having any remanence, i.e., B(0)=0.

These materials may be in the form of particles of nanometric dimensions (i.e., the large diameter of which is between a few nanometers and a few tens of nm), for example, nanoparticles of Fe, Ni or Co, or other mixtures. The nanoparticles may be incorporated into magnetic microbeads of micrometric dimensions by way of a binder.

A number of applications make use of the linear and/or non-linear characteristics of such magnetic microbeads. This is the case in particular in the field of immunoassay.

Thus, the document US2009243603 discloses a device for measuring an amount of superparamagnetic material (referred to more simply as "magnetic mass" in the remainder of this description). The mass is that of the nanoparticles contained in the microbeads combined with an analyte of a liquid sample. The liquid solution is arranged on an analysis medium formed, for example, of a strip of porous material, as is well known per se in the field.

The measuring device proposed by this document is formed of four planar coils arranged in a measuring bridge on a printed circuit board (PCB). A measuring coil is thus connected in series with a reference coil to form a first branch of the bridge. The two other coils, also interconnected in series, form a compensation branch, arranged in parallel with the first branch.

A test zone of the strip of materials comprising the magnetic microbeads is arranged to the right of the measuring coil. A high-frequency signal is injected into the measuring bridge, and the magnetic field produced by the measuring coil is used for magnetizing the magnetic particles. These magnetic particles interact with the measuring coil to modify the magnetic field, and thus indirectly its inductance. This modification can be measured by way of a voltage measured between two measuring points, the voltage having the same high frequency as that of the signal injected, in order to estimate the magnetic mass present in the measuring zone.

The measuring device proposed by this document is advantageous in that it makes it possible to estimate the difference of the magnetic masses arranged, respectively, in the region of the measuring coil and in the region of the reference coil. Appropriately arranging the strip, forming the analysis medium, to the right of the measuring coil and to the right of the reference coil makes it possible to estimate the difference of the magnetic masses arranged, respectively, in the two regions of the strip. It is thus possible to measure the difference between the magnetic mass present in a measuring zone of the strip and the residual magnetic mass present outside of the zone, in a non-specific zone of the strip referred to as the migration zone.

It is nonetheless noted that the measuring device proposed by this document is particularly imprecise in a real environment. Indeed, it is very sensitive to external disturbances and to instabilities of its excitation source; thus, its detection limit is not very satisfactory in these conditions. It uses microbeads comprising superparamagnetic particles, but does not make use of the non-linear characteristics of these particles.

The document EP3314248 in turn makes use of the non-linear superparamagnetic properties of the particles, for example, incorporated into the microbeads, in order to provide a much more reliable measurement of the magnetic mass of these particles. The measuring device comprises four coils, one of which is a measuring coil in which the amount of material to be measured is placed.

The four coils are arranged electrically in series, and are identical to one another. High-frequency (HF), low-frequency (BF), and direct (DC) currents pass through the coils, according to a very precise configuration intended to develop a different magnetic field in each of the coils. The superparamagnetic material is exposed to a high-frequency and a low-frequency magnetic field, and, on account of the non-linear behavior of the material, the response to this excitation contains components at frequencies that are linear combinations of the excitation frequencies. The document provides for measuring a measuring voltage component at a frequency that corresponds to the frequency HF−BF and/or HF+BF. The component becomes proportional to the amount of superparamagnetic material arranged in the measuring coil, when a DC component is applied in addition. This amount reverses when the DC component is reversed, which makes it possible to improve the signal-to-noise ratio of the measurement, when an excitation sequence having a plurality of DC component values (in general having an average value of zero) is performed.

The measurement provided by this device is particularly sensitive, in particular, when the measurement is reproduced for a plurality of DC currents, which are different from one another, as is set out in the document EP3314248.

However, the measuring device does not make it possible to measure a difference in magnetic masse between two measuring zones. Indeed, the "series" topology of the coils and the design selection aiming to provide a different magnetic field in each of the coils lead, systematically, to adding the magnetic masses, which would be arranged in the coils, whatever the couple of coils in question. Moreover, the magnetic couplings between the close coils are formed by adding and/or subtracting the fields, which creates asymmetry of the resulting fields and leads to coil sensitivities that are very different from one another. In order to prevent the creation of "dead zones" between or in the coils, it is necessary to physically distance the coils from one another, or indeed to use the symmetrical topology as described in the document EP3314248, which reinforces the impossibility of forming a compact differential device.

BRIEF SUMMARY

One aim of the disclosure is that of proposing a measuring device, which overcomes the above-mentioned disadvantages, at least in part. It aims, in particular, to provide a measuring device, which makes it possible to provide a reliable, and differential, measurement of magnetic masses arranged, respectively, in two different zones of an analysis medium.

With this aim in mind, the present disclosure proposes a device for measuring an amount of superparamagnetic material, the device comprising:

a first branch comprising a first coil and a second coil, which are mounted in series in the region of a first midpoint and a second branch, mounted in parallel with the first branch and comprising a third coil and a fourth coil, which are mounted in series in the region of a second midpoint, the first coil and the third coil forming a pair of measuring coils, the second coil and the fourth coil forming a pair of compensating coils, the coils of a pair being identical to each other;

at least one direct current generator of a current having a first frequency, referred to as a low-frequency generator, and a current having a second frequency, which is greater than the first frequency, referred to as a high-frequency generator, the generators being coupled to the first and second branches to inject into each of the coils a current having a DC component, a component having a first frequency, and a component having a second frequency, such that the magnetic fields generated by the coils of the same pair are identical;

a detector of a component of an electric voltage present between the midpoint of each branch, the component being set at a mixing frequency, which is a linear combination of the first and the second frequency.

According to other advantageous and non-limiting features of the present disclosure, taken individually or in any technically possible combination:

the two pairs of coils are arranged, in the device, so as to be symmetrical with respect to a reference plane;
the at least one generator is formed by a bridge arm;
the coils are formed by conductor tracks arranged on a planar insulating support;
the coils are arranged on the planar insulating support along the same line;
the coils are arranged on the planar support at the four corners of a rectangle;
the coils are formed by a winding of a conductive wire around a central cylinder;
the coils of the same pair are arranged one on top of the other, the respective central cylinders thereof being aligned;
the pair of compensating coils is formed by a winding of a pair of conductive wires around a single central cylinder;
the measuring device comprises shielding, which makes it possible to protect the coils from external electromagnetic fields, at least in part;
the measuring device comprises a receptacle for receiving an analysis medium;
the receptacle and the coils of the measuring pair are arranged such that a test zone of the analysis medium is located in the region of the first coil, and a migration zone of the analysis medium is located in the region of the third coil.

According to another aspect, the present disclosure proposes a method for measuring an amount of superparamagnetic material arranged on an analysis medium, the method comprising:

a placement step, intended to arrange the analysis medium simultaneously on the first coil and on the third coil of the pair of measuring coils of a measuring device as described above;
a measuring step, intended for performing at least one measurement of the difference of the amounts of material arranged on the analysis medium to the right of the first coil and to the right of the second coil, respectively.

Advantageously, the analysis medium is moved relative to the coils of the pair of measuring coils, and the measuring step is repeated in order to provide a succession of measurements.

BRIEF DESCRIPTION OF THE DRAWINGS

Other features and advantages of the present disclosure will become clear from the following detailed description of the present disclosure, with reference to the accompanying drawings, in which.

DETAILED DESCRIPTION

In a general manner, a device according to the present disclosure is provided with an electronic portion and a measuring head, the measuring head comprising a receptacle that is designed to receive an amount of superparamagnetic material, the mass of which is intended to be estimated. As is described in the European patent EP3314248, this estimation is achieved by comparing a measurement vector of the amount of material with a pre-established signature vector of a reference amount of the material.

When the device is designed for an application in the field of immunology, the receptacle is designed to receive an analysis medium. This analysis medium may take the form of a column filled with a porous material, or a test strip also formed by a porous material of this kind, facilitating the capillary migration of a liquid sample, laterally on the strip.

The measuring device of the present description is more particularly suitable for an analysis medium of this kind, present in the form of a test strip.

Figure 1:
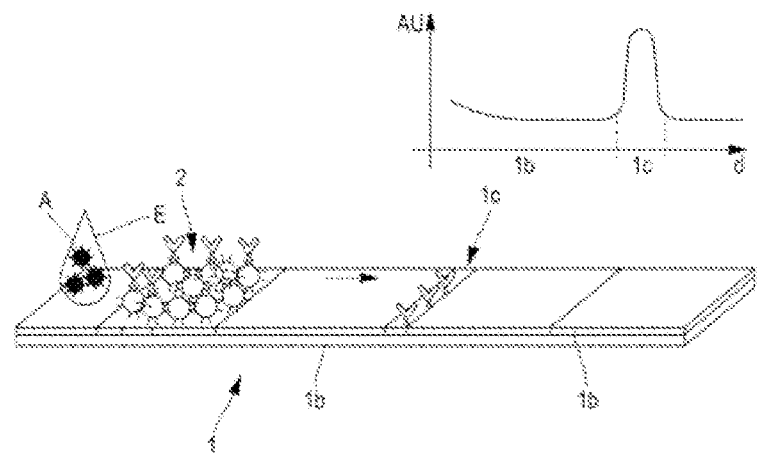
FIG. 1 shows a test strip of the prior art in the field of immunoassay.

It is noted that, with reference to FIG. 1, in the field of immunology the sample E, likely to contain an analyte A, is brought together with magnetic microbeads 2 comprising superparamagnetic particles, these magnetic microbeads 2 being functionalized so as to bind to the analyte of the sample. The strip 1 comprises a functionalized test zone 1c for retaining the analyte A bound to the magnetic microbeads. The part 1b of the strip, which contributes to the migration of the sample as far as the test zone 1c, and beyond the zone, is generally referred to by the expression "non-specific migration zone." It is not intended to retain the analyte A or the other elements contained in the sample, but residues of the elements may nonetheless be present (and, in particular, magnetic microbeads 2 bound, or not, to the analyte). Thus, the insert of FIG. 1 shows the amount of magnetic microbeads 2 (on the Y-axis and in arbitrary units) distributed along the strip (on the X-axis). A peak in the amount is observed in the region of the test zone 1c, and a gradient is observed along the migration zone 1b, in the flow direction of the liquid sample E. In order to make the best estimation of the amount of analyte present in the sample, or in order to detect the presence of the analyte, it is therefore advantageous to measure the difference in the magnetic masses present in the test zone 1c and in the migration zone 1b, respectively.

A device according to the present description makes it possible to perform a differential measurement of this kind. Thus, and with reference to FIG. 2, a device 10 of this kind comprises four coils arranged in the following manner: in a first branch, a first coil P1A and a second coil P2A are mounted in series, in the region of a first midpoint M1. In a second branch, mounted in parallel with the first branch, a third coil P1B and a fourth coil P2B are mounted in series, in the region of a second midpoint M2. The first coil P1A and the third coil P1B form a pair of measuring coils P1, the second coil P2A and the fourth coil P2B form a pair of compensating coils P2.

The coils of a pair P1, P2 are identical to one another. Furthermore, the two pairs of coils P1, P2 are identical to one another and are arranged, in the preferred embodiments of a device 10 according to the present disclosure, so as to be symmetrical with respect to a reference plane. In this way, it is ensured that the high-frequency components of the fields generated by each of the pairs of coils (which are of opposing signs, as will be set out in detail in the remainder of this disclosure) keep their intensities and their oppositions, despite the magnetic coupling, which may take place between the two pairs. The device is thus less sensitive to its electromagnetic surroundings. In these preferred embodiments, the two pairs of coils P1, P2 may be integrated in a compact manner in the measuring head of the device 10.

In an advantageous manner, and as will be made clear in the remainder of this disclosure, the measuring medium receptacle is arranged to the right of (or in) the pair of measuring coils P1. That is to say that, when the analysis medium is placed in or on the receptacle, it is directly exposed to the magnetic fields generated by the measuring coil P1A and by the reference coil P1B.

The measuring device 10 is also provided, in the electronic portion thereof, with at least one generator associated with the different coils, so as to inject currents in the assembly, which has just been described. More specifically, the measuring device 10 comprises:
- a generator GDC for generating DC current IDC, i.e., generating a DC current IDC, which is quasi static and in any case has a frequency of less than 100 Hz;
- a generator GBF for generating low-frequency current IBF, the frequency (the first frequency BF) of which is typically between 100 Hz and 10 kHz;
- a generator GHF for generating high-frequency current IHF, the frequency (the second frequency HF) of which is typically between 10 kilohertz and 1 MHz.

Preferably, the frequency ratio between each of these generators is greater than 10, in order to clearly separate the currents from one another, in terms of frequency. The spectrum of the current signals provided by these generators may be made up of a single line or may cover a more complete band, in particular, in the respective intervals cited above.

These generators may be implemented by one or a plurality of bridge arms, controlled by a pulse width modulation signal, which makes it possible to selectively switch a load RLC a supply voltage and a mass in order to form the current having controlled intensity and frequency properties. These generators are, in particular, those described in the prior art document EP3314248.

The generators GDC, GBF, GHF are coupled to the first and second branches to inject into each of the coils P1A, P1B, P2A, P2B a current having a DC component, a component having a first frequency BF, and a component having a second frequency HF, such that the magnetic fields generated by the coils of the same pair P1, P2 are identical. More precisely, the magnetic fields produced by the first coil P1A and the third coil P1B are mutually identical, and the magnetic fields produced by the second coil P2A to the fourth coil P2B are mutually identical.

Since the coils of each pair P1, P2 are mutually identical, this condition amounts to positing that the currents passing, respectively, through the coils of the same pair are also mutually identical.

It is thus possible to provide, according to a first configuration, for the current passing through the coils P1A, P1B of the first pair P1 to be equal to IDC+IBF+IHF, and for the current passing through the coils P2A, P2B of the second pair P2 to be equal to IDC+IBF−IHF.

In a second configuration, the current passing through the coils P1A, P1B of the first pair P1 is equal to IDC+IBF+IHF, and the current passing through the coils of the second pair P2 is equal to IDC−IBF+IHF.

In yet another configuration, the current passing through the coils P1A, P1B of the first pair P1 is equal to IDC+IBF+IHF, and the current passing through the coils of the second pair P2 is equal to −IDC+IBF+IHF. Many other configurations are of course possible, which make it possible to comply with the condition according to which the magnetic fields produced by the coils of each pair P1, P2 are identical.

Advantageously combined with the requirement for symmetry with respect to a reference plane, set out above, this configuration makes it possible to reliably measure a difference in the magnetic mass.

Figure 2:
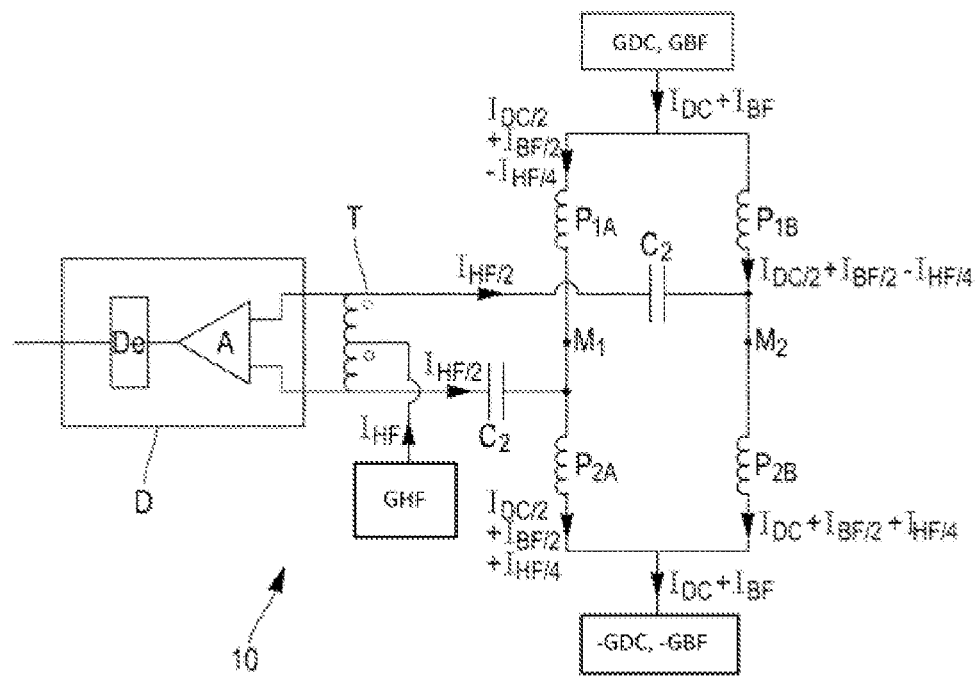
FIG. 2 is a flow diagram of a measuring device according to the present disclosure.

FIG. 2 thus shows a measuring device 10 for which the generators GDC, GBF, GHF are connected to the coils according to the first configuration set out above.

The generator GDC for generating DC current IDC, and the generator GBF for generating low-frequency current IBF are thus designed to inject a current flowing in each branch, and successively in the coils of the first and of the second pair P1, P2. In the assembly shown, two generators GDC for generating DC current IDC and two generators GBF for generating low-frequency current IBF have been provided, which are selectively actuated according to whether it is intended to generate a current flowing in one direction of the branches (+IDC, +IBF) or whether it is intended to generate a current flowing in the other direction of the branches (−IDC, −IBF).

In turn, the generator GHF for generating high-frequency current IHF injects, via a common mode inductor T, a current in the region of the midpoints M1, M2 of the two branches. The equal nature of the current flowing in the coils of the pair of measuring coils and of the pair of compensating coils can be clearly confirmed in FIG. 2. As is also shown in FIG. 2, it is also possible to provide decoupling capacitors C2 between the high-frequency generator GHF and the remainder of the circuit.

The measuring device 10 finally comprises a voltage detector D (electromotive force) between two measurement terminals, in this case arranged, respectively, at the midpoints M1, M2 of the branches. The voltage detector D identifies a voltage component at a mixing frequency.

The mixing frequency is a linear combination of the first frequency BF and of the second frequency HF. "Linear combination" means the combination of these frequencies with integer, fixed and unprejudiced coefficients. The mixing frequency can thus correspond, by way of example, to the frequency HF−BF and/or to the frequency HF+BF.

The detector D can, in particular, be that described in detail in the document EP3314248. It comprises, for example, a differential amplifier A located between the 2 terminals of the common mode inductor T, making it possible to recover the voltage present between the two measuring terminals and at least one demodulator De of the amplified signal, in order to extract therefrom the component at the mixing frequency. The signal provided at the output of the detector D forms the measurement provided by the device 10.

When an amount of superparamagnetic material is positioned opposite a coil of the measuring pair P1, as will be described in detail in the following, the non-linear behavior of this material, when it is exposed to a sufficiently intense high-frequency and low-frequency field, results in components at the mixing frequencies. The amplitude of these components is proportional to the amount of material positioned opposite the coil at the origin of the field. When two amounts of superparamagnetic material are positioned opposite the measuring coil and the reference coil, respectively, these amounts affect the voltages, which develop at the midpoints in the same way, such that the voltage taken off between these two measuring points, after processing by the detector D, indeed represents the difference in the amounts of materials.

Advantageously, the four coils are arranged in a housing of the measuring device 10, which defines, for example, the measuring head of the device 10, and which forms shielding by a transformation effect of a shorting turn (the shielding acts as a shorting turn). The coils are thus protected from the external electromagnetic fields around the frequency HF, which could interfere with the measurement. The fact of placing the 4 coils in this same shielding makes it possible to eliminate the external fields, without, however, attenuating the HF excitation fields: indeed, the HF fields of the 2 pairs cancel one another out, and are not affected by the shorting turn.

The principles that have just been set out may be implemented according to different embodiments.

Thus, and according to a first embodiment referred to as "planar," the coils are formed by conductor tracks arranged on a planar insulating support (such as a printed circuit board). The support may be multi-layer and incorporate, in particular, shielding turns in addition to or instead of the shielding housing mentioned above.

Figure 3A:
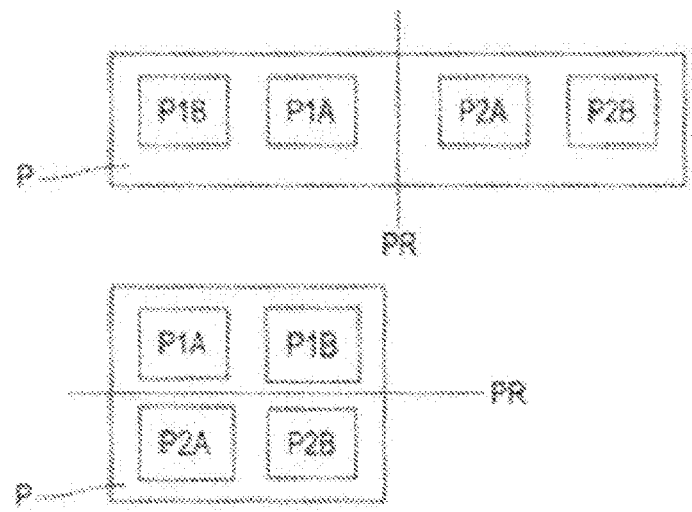
FIGS. 3a and 3b schematically show two embodiments of the measuring device according to the present disclosure.

As is shown schematically in FIG. 3a, the coils may be arranged on the planar support P along the same line or at the four corners of a rectangle, while complying with the symmetry with respect to a reference plane PR, as has been proposed above.

In order to perform a measurement of an analysis medium (which may be in the form of a test strip), during a placement step the analysis medium is arranged simultaneously on the first coil P1A and on the third coil P1B of the pair of measuring coils P1. More precisely, it is intended to arrange the test zone 1c of the test strip to the right of the first coil P1A of the measuring pair P1, and to simultaneously place the migration zone 1b of the strip to the right of the third coil P1B. This arrangement of the analysis medium may be guided by the positioning of the receptacle. It would nonetheless be possible to provide a reverse configuration, without affecting the general operation of the measuring device.

In order to facilitate the correct positioning of the analysis medium, it would be possible to arrange the coils of the measuring pair P1 on the support such that the distance separating them is compatible with the selected configuration of the test strip. It will, in particular, be ensured that the dimensions of the coils correspond sufficiently to the dimensions of the different zones of the analysis medium, such that the measurement is not adversely affected by the presence of magnetic masses arranged on the zones adjacent to the test and migration zones.

Figure 3B:
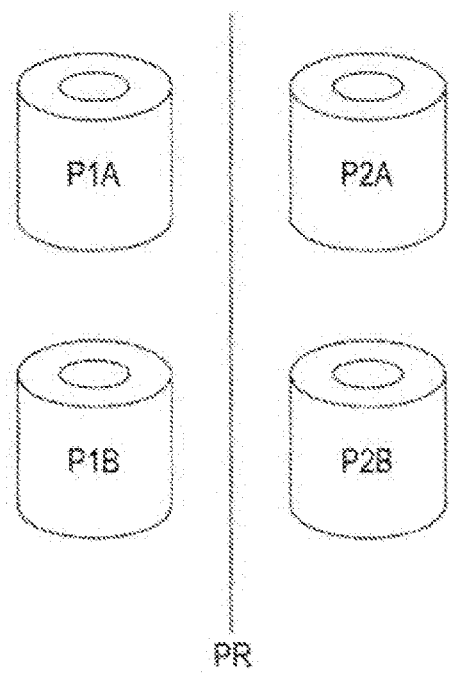

According to another embodiment, referred to as "volumetric," shown in FIG. 3b, the coils of the measuring device 10 are formed by a winding of a conductive wire on a central cylinder. The central cylinder may be hollow, in particular, for the coils forming the measuring pair P1, so as to be able to place the analysis medium therein.

The coils of the same pair are arranged one on top of the other, the cylinders thereof being aligned with one another. The 2 pairs are placed in parallel with one another, and thus the requirement of symmetry with respect to a reference plane PR is complied with.

In this embodiment, the analysis medium is intended to be arranged at the center of the coils, in the hollow cylinders of the first coil P1A and/or of the third coil P1B. More precisely, it is possible to seek to arrange the test zone 1c of a test strip, forming the analysis medium, in the central cylinder of the first coil P1A, and the migration zone 1b of the test strip in the central cylinder of the third coil P1B. A reverse configuration is of course possible.

The same precautions as those mentioned in the planar embodiment are to be taken with regard to the geometry and the placement of the coils with respect to the selected configuration of the test strip.

It is noted that the symmetrical arrangement of the two pairs of measuring P1 and compensating coils P2 does not form an essential condition allowing for the operation of a device 10 according to the present disclosure. In some cases, it may be preferable to deviate from this arrangement. It may thus be possible to choose to arrange only the measuring pair P1 in the measuring head, and to arrange the compensating pair so as to be at a distance from the head (for example, of more than 10 cm), for example, in order to integrate it into the electronic portion of the device 10. This distancing of the two pairs of coils may lead to the requirement of symmetry not being complied with, while proposing a device that is entirely functional, in particular, when the electromagnetic environment of the device is controlled, as may be the case in a laboratory.

When the requirement of symmetry is not essential, it is possible to simplify the design of the pair of compensating coils P2 by forming the pair by way of a winding of a pair of conductive wires (for example, a pair of twisted conductive wires) around a single central cylinder. The ends of each conductive wire of the pair are electrically connected, in accordance with the flow diagram of FIG. 2. In this case, the second coil P2A and the fourth coil P2B, which form the pair of compensating coils P2, are integrated into one another, as it were, which makes the compensating pair P2 particularly compact and the coils P2A and P2B particularly identical. In this non-symmetrical embodiment, the measuring pair P1 may be, interchangeably, of the planar or volumetric type.

The measuring principles exploited in the various embodiments of the device 10, which have just been set out are identical to those proposed in the document EP3314248, and for the sake of brevity are not described in detail here. After the analysis medium has been appropriately positioned with respect to the pair of measuring coils, as has been shown above, a plurality of measurements of the magnetic mass to be estimated are performed, these measurements being indexed by distinct DC current IDC values. These measurements are then combined to form a measurement vector. The measurement vector is itself combined with a signature vector of a standard magnetic mass, as has been specified in the introductory part of this application, for estimating the mass of the amount of superparamagnetic material. This combination can, in particular, implement a scalar product of the two vectors.

As has been seen, and in contrast with the measuring method described in the prior art document, the device 10 may make it possible, after the step of placement of the analysis medium into the receptacle, to perform a measuring step, intended for performing at least one measurement of the difference of the amounts of material arranged on the analysis medium to the right of the first coil P1A and to the right of the second coil P1B, respectively.

This principle may be exploited according to a particularly advantageous embodiment of the measuring method, according to which the measuring medium is caused to move in the receptacle, i.e., to the right of the coils of the measuring pair P1 or in the hollow cylinders of the coils. The embodiment provides for performing a measurement (and more precisely for acquiring a measurement vector for different values of the DC current ICD) in a plurality of positions of the analysis medium. It may, for example, be a case, when the medium is in the form of a test strip, of causing the strip (the "scanner") to move above the coils or inside these, according to the "planar" or "volumetric" embodiment selected.

By way of example, it is possible, during a first measurement, to position the test zone 1c of the test strip in the center of or to the right of the first coil P1A, and then to cause the strip to move so as to position the test zone 1c, with the aim of a second measurement, in the center of or to the right of the third coil P1B.

The first differential measurement will correspond to the magnetic mass in the region of the test zone 1c (in the region of the first coil P1A) subtracted from the "background noise" magnetic mass present in the migration zone 1b (in the region of the third coil P2A).

The second differential measurement will correspond to a "background noise" magnetic mass present in the migration zone 1b arranged on the other side of the test zone 1c (now in the region of the first coil P1A) subtracted from the magnetic mass present in the test zone 1c (now in the region of the third coil P1B).

Adding these to measurements, and averaging them, gives a much more precise measurement of the magnetic mass present in the test zone 1c. It is possible to generalize this principle by repeating the measurements during the course of the movement of the test strip.

Of course, the present disclosure is not limited to the embodiments described, and it is possible to add variants thereto, without extending beyond the scope of the invention as defined by the claims.

The invention claimed is:

1. A device for measuring an amount of superparamagnetic material, the device comprising:
    a first branch comprising a first coil and a second coil, which are mounted in series in a region of a first midpoint, and a second branch, mounted in parallel with the first branch and comprising a third coil and a fourth coil, which are mounted in series in the region of a second midpoint, the first coil and the third coil forming a pair of measuring coils, the second coil and the fourth coil forming a pair of compensating coils, the coils of a pair being identical to each other;
    at least one direct current generator of a current having a first frequency, referred to as a low-frequency generator, and a current having a second frequency, which is greater than the first frequency, referred to as a high-frequency generator, the generators being coupled to the first and second branches to inject into each of the coils a current having a DC component, a component having a first frequency, and a component having a second frequency, such that magnetic fields generated by the coils of the same pair are identical; and
    a detector of a component of an electric voltage present between the midpoint of each branch, the component being set at a mixing frequency, the mixing frequency being a linear combination of the first and the second frequency.

2. The device of claim 1, wherein the two pairs of coils are arranged in the device so as to be symmetrical with respect to a reference plane.

3. The device of claim 1, wherein the at least one direct current generator comprises a bridge arm.

4. The device of claim 1, wherein the coils comprise conductor tracks arranged on a planar insulating support.

5. The device of claim 4, wherein the coils are arranged on the planar insulating support along the same line.

6. The device of claim 4, wherein the coils are arranged on the planar insulating support at the four corners of a rectangle.

7. The device of claim 1, wherein the coils comprise a winding of a conductive wire around a central cylinder.

8. The device of claim 7, wherein the coils of the same pair are arranged one on top of the other, the respective central cylinders thereof being aligned.

9. The device of claim 7, wherein the pair of compensating coils comprises a winding of a pair of conductive wires around a single central cylinder.

10. The device of claim 1, further comprising shielding located and configured to at least partially protect the coils from external electromagnetic fields.

11. The device of claim 1, further comprising a receptacle configured to receive an analysis medium therein.

12. The device of claim 11, wherein the receptacle and the coils of the measuring pair are arranged such that a test zone of the analysis medium is located in the region of the first coil, and a migration zone of the analysis medium is located in the region of the third coil.

13. A method for measuring an amount of superparamagnetic material on an analysis medium, the method comprising:
    a placement step comprising arranging the analysis medium simultaneously on the first coil and on the third coil of the pair of measuring coils of a measuring device according to claim 1; and
    a measuring step comprising performing at least one measurement of a difference of amounts of material arranged on the analysis medium adjacent the first coil and adjacent the second coil, respectively.

14. The method of claim 13, further comprising iteratively moving the analysis medium relative to the coils of the pair of measuring coils, and repeating the measuring step to provide a succession of measurements.

15. The device of claim 2, wherein the at least one direct current generator comprises a bridge arm.

16. The device of claim 15, wherein the coils comprise conductor tracks arranged on a planar insulating support.

17. The device of claim 15, wherein the coils comprise a winding of a conductive wire around a central cylinder.

18. The device of claim 15, further comprising shielding located and configured to at least partially protect the coils from external electromagnetic fields.

19. The device of claim 18, further comprising a receptacle configured to receive an analysis medium therein.

20. The device of claim 19, wherein the receptacle and the coils of the measuring pair are arranged such that a test zone of the analysis medium is located in the region of the first coil, and a migration zone of the analysis medium is located in the region of the third coil.

* * * * *